(12) United States Patent
Guofang et al.

(10) Patent No.: US 6,761,981 B2
(45) Date of Patent: Jul. 13, 2004

(54) CYCLIC TERTIARY AMINE COMPOUND AND ORGANIC ELECTROLUMINESCENT DEVICE CONTAINING THE COMPOUND

(75) Inventors: Wang Guofang, Yokohama (JP); Manabu Uchida, Yokohama (JP); Hajime Yokoi, Yokohama (JP); Takaharu Nakano, Yokohama (JP); Kenji Furukawa, Yokohama (JP)

(73) Assignee: Chisso Corporation, Osaka (JP)

( * ) Notice: Subject to any disclaimer, the term of this patent is extended or adjusted under 35 U.S.C. 154(b) by 34 days.

(21) Appl. No.: 09/965,589

(22) Filed: Sep. 26, 2001

(65) Prior Publication Data

US 2002/0058155 A1 May 16, 2002

(30) Foreign Application Priority Data

Sep. 28, 2000 (JP) ........................... 2000-297209
Jun. 26, 2001 (JP) ........................... 2001-193511

(51) Int. Cl.$^7$ ............................................. H05B 33/12
(52) U.S. Cl. .................. 428/690; 428/917; 313/504; 313/506
(58) Field of Search .................. 428/690, 917; 313/504, 506; 252/301.16; 540/450, 470, 474; 564/305, 426, 429, 431, 433, 434

(56) References Cited

U.S. PATENT DOCUMENTS

| | | | |
|---|---|---|---|
| 4,047,948 A | 9/1977 | Horgan | |
| 4,536,457 A | 8/1985 | Tam | |
| 4,539,507 A | 9/1985 | VanSlyke et al. | 313/504 |
| 5,047,687 A | 9/1991 | VanSlyke | 313/503 |
| 5,061,569 A | 10/1991 | VanSlyke et al. | 428/457 |

FOREIGN PATENT DOCUMENTS

| | | |
|---|---|---|
| EP | 0 508 562 A1 | 10/1992 |
| EP | 0 517 542 A1 | 12/1992 |
| EP | 0 611 148 A1 | 8/1994 |
| EP | 0 650 955 A1 | 5/1995 |
| EP | 0 666 298 A2 | 8/1995 |
| EP | 0 731 625 A2 | 9/1996 |
| JP | 5-239455 | 9/1993 |
| JP | 6-32307 | 4/1994 |
| JP | 8-87122 | 4/1996 |
| JP | 9-194441 | 7/1997 |

OTHER PUBLICATIONS

Chihaya Adachi, et al., Confinement of charge carriers and molecular excitons within 5–nm–thick emitter layer in organic electroluminescent devices with a double heterostructure, Appl. Phys. Lett. 57 (6), Aug. 6, 1990, pp. 57–59.
Yoshiyuki Kuwabara, et al., Thermally Stable Multilayered Organic Electroluminescent Devices Using Novel Starburst Molecules, 4,4',4"–Tri(N–carbazolyl)triphenylamine (TCTA) and 4,4',4"–Tris(3–methylphenylphenyl–amino)triphenylamine (m–MTDATA), ad Hole–Transport Materials, Advanced Materials, 1994, 6 No. 9., 677–679, no month.
Hiromitsu Tanaka, et al., Novel hole–transporting materials based on triphenylamine for organic electroluminescent devices, Chem. Commun, 1996, pp. 2175–2176, no month.
Sheila I Hauck, et al., Tetraazacyclophanes by Palladium–Catalyzed Aromatic Amination. Geometrically Defined, Stable, High–Spin Diradicals, Organic Letters vol. 1 No. 13, 2057–2060, published on web Nov. 25, 1999.
T D Selby and S C Blackstock, "Macrocyclic Poly Arylamines for Rigid Connection of Poly Radical Cation Spins", Cas–Online Abstract Accession No. 1999:699801 & Org. Lett. vol. 1, No. 13, 1999, p. 2053–2055 (published on web Nov. 3, 1999).

*Primary Examiner*—Marie Yamnitzky
(74) *Attorney, Agent, or Firm*—Knobbe, Martens, Olson & Bear, LLP

(57) ABSTRACT

A cyclic tertiary amine compound represented by a formula (1) and an organic luminescent device are disclosed. Use of the cyclic tertiary amine compound as a hole transport material, a hole injection material or an organic electroluminescent material can provide organic EL devices having high luminous efficiency and a long service life.

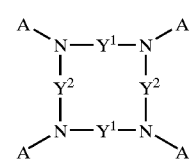

(1)

4 Claims, No Drawings

CYCLIC TERTIARY AMINE COMPOUND AND ORGANIC ELECTROLUMINESCENT DEVICE CONTAINING THE COMPOUND

BACKGROUND OF THE INVENTION

1. Field of the Invention

The present invention relates to novel cyclic tertiary amine compounds and to organic electroluminescent devices (hereinafter abbreviated as "organic EL devices") using the compounds.

2. Description of the Related Art

Recently, organic EL devices have been given much attention as a full color flat panel display of next generation and vigorous research and development thereon have been under way. The organic EL devices are injection type luminous devices that have two electrodes sandwiching a luminescent layer therebetween. They emit light when electrons and holes are injected into an organic luminescent layer to be recombined therein. The material that can be used includes low molecular weight materials and high molecular weight materials. Both of them are proved to give organic EL devices with high luminance.

Such organic EL devices include two types. One type uses an electron transport material containing a fluorescent dye disclosed by C. W. Tang, et al. (J. Appl. Phys., 65, 3610 (1989)) as a luminescent layer. Another type uses a fluorescent dye itself as a luminescent layer (for example, the device described in Appl. Phys. 27, L269 (1988)).

The type that uses a fluorescent dye as a luminescent layer is roughly divided into 3 sub-types. The first sub-type includes a three-layer structure having an electron transport layer and a hole transport layer sandwiching a luminescent layer therebetween. The second sub-type includes a two-layer structure having a hole transport layer and a luminescent layer laminated one on another, and the third sub-type includes a two-layer structure having an electron transport layer and a luminescent layer laminated one on another. These laminate structures are known to improve the luminous efficiency of organic EL devices.

The electron transport layer in the organic EL device of the above-mentioned structure contains an electron transport compound and has a function of transporting electrons injected from the cathode to the luminescent layer. The hole transport layer and hole injection layer are layers that contain hole transport compounds, respectively, and have functions of transporting holes injected from the anode to the luminescent layer. Interposition of the hole injection layer between the anode and the luminescent layer enables transport of many holes from the anode to the luminescent layer at a low electric field and further enables confinement of electrons injected from the electron transport layer or electron injection layer within the luminescent layer. This can give rise to organic EL devices having excellent luminescent ability such as increased luminous efficiency.

However, these organic EL devices do not have enough performance sufficient for practical use. The major reason therefor is insufficient durability of the material used, and in particular, poor durability of the hole transport material. Heterogeneous portion such as grain boundary, if any, in the organic layer in an organic EL device causes the concentration of the electric field in that portion, which may lead to the deterioration or breakage of the device. Therefore, the organic layer is used mostly in an amorphous state. Also, the hole transport property of the hole transport material was insufficient so that the luminous efficiency of the device was insufficient for practical use.

Although various materials centered on triphenylamine derivatives have been known as the hole transport material used in such organic EL devices as described above, there are only few materials that are suitable for practical use. For example, N,N'-diphenyl-N,N'-di(3-methylphenyl)-4,4'-diaminobiphenyl (hereinafter abbreviated as "TPD") has been reported (Appl. Phys. Lett. 57,6,531(1990)). However, this compound is poor in thermal stability and causes a problem in the service life of the device containing it. Many triphenylamine derivatives are disclosed in U.S. Pat. Nos. 5,047,687, 4,047,948 and 4,536,457, Japanese Patent Publication No. Hei 6-32307, Japanese Patent Application Laid-open Nos. Hei 5-234681, Hei 5-239455, Hei 8-87122 and Hei 8-259940. However, none of the compounds have sufficient properties.

Among the amine derivatives disclosed in Japanese Patent Application Laid-open Nos. Hei 4-308688 and Hei 6-1972 and Adv. Mater., 1994, 6, No. 9, p.677, which are called starburst molecules by the authors based on the structures of the compounds, and also among the compounds disclosed in Japanese Patent Application Laid-open Nos. Hei 7-126226, Hei 7-126615, Hei 7-331238, Hei 7-97355, Hei 8-48656, Hei 8-100172 and Hei 9-194441 and J. Chem. Soc. Chem. Comm., 2175 (1996), there has been none that has practically indispensable property of having a long service life with high luminous efficiency. Org. Lett., 1, 13, 2057 (1999) discloses tetraazacyclophane derivatives. However, the literature contains no description that they are useful as a material for organic EL devices.

As described above, the hole transport materials used in conventional organic EL devices do not have practically sufficient performances and hence it has been desired to increase the efficiency and the service life of the organic EL devices by using excellent materials. Further, in the most organic EL devices, the luminescence is provided by the luminescent layer or electron transport layer separately arranged from a charge transport layer, but in few cases by the hole transport layer. The reason for this is considered that a luminescence color of the hole transport material itself and intensity of luminescence are regarded as important factors although there may also exist the problem of compatibility of the hole transport layer with the electron transport layer used simultaneously. It is anticipated that a layer that functions as a hole transport layer and at the same time as a luminescent layer, if any, will have a high practical value. However, few such materials have been known. Inmost cases, such materials have long emission wavelengths, and short wavelength emission cannot be obtained.

SUMMARY OF THE INVENTION

The inventors of the present invention have made extensive studies with a view of solving the above-mentioned problems inherent in conventional organic EL devices. As a result, they have found out that use of specific cyclic tertiary amine compounds can give rise to organic EL devices that have high efficiency and long service life. The present invention has been achieved based on the finding.

That is, the present invention is composed by the followings.

(1) A cyclic tertiary amine compound represented by a formula (1)

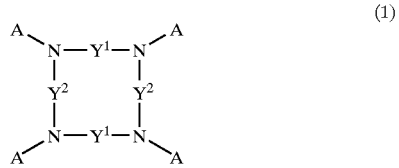

(1)

wherein A represents an alkyl group having 1 to 6 carbon atoms, a substituted or unsubstituted aryl group, a substituted or unsubstituted aralkyl group, or a substituted or unsubstituted heterocyclic group, and four As may be all the same or partly different; $Y^1$ represents a substituted or unsubstituted arylene group, or a substituted or unsubstituted heterocyclic divalent group; $Y^2$ represents a group represented by a formula (2), a substituted or unsubstituted condensed ring arylene group, or a substituted or unsubstituted heterocyclic divalent group,

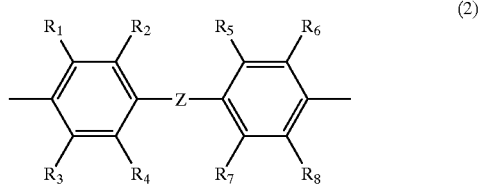

(2)

wherein $R_1$ to $R_8$ in the formula (2) independently represents a hydrogen atom, a halogen atom, an alkyl or alkoxy group having 1 to 6 carbon atoms, an aryl group or a heterocyclic group; and Z represents single bond, an arylene group, —CH$_2$—, —CH=CH—, —C≡C—, —C(CH$_3$)$_2$—, —CO—, —O—, —S— or —SO$_2$—.

(2) An organic electroluminescent device comprising a cyclic tertiary amine according to the above item (1).
(3) An organic electroluminescent device according to the above item (2), wherein the cyclic tertiary amine compound according to the above item (1) is contained in a hole transport layer.
(4) An organic electroluminescent device according to the above item (2), wherein the cyclic tertiary amine compound according to the above item (1) is contained in a luminescent layer.
(5) An organic electroluminescent device according to the above item (2), wherein the cyclic tertiary amine compound according to the above item (1) is contained in a hole injection layer.
(6) An organic electroluminescent material comprising a cyclic tertiary amine compound according to the above item (1).
(7) A hole transport material comprising a cyclic tertiary amine compound according to the above item (1).

DETAILED DESCRIPTION OF PREFERRED EMBODIMENTS

Hereinafter, the present invention will be described in detail.

The symbol "A" in the formula (1) is an alkyl group having 1 to 6 carbon atoms, a substituted or unsubstituted aryl group, substituted or unsubstituted aralkyl group, or a substituted or unsubstituted heterocyclic group. Specific examples of these groups include methyl, ethyl, n-propyl, n-butyl, n-hexyl, phenyl, tolyl, xylyl, biphenyl, naphthyl, anthryl, phenanthryl, benzyl, phenylethyl, methylbenzyl, naphthylmethyl, furyl, thienyl, benzofuranyl, benzothiophenyl, indolyl, isoindolyl, chromenyl, isochromenyl, quinolyl, isoquinolyl and naphthothiophenyl. Of these groups, phenyl, tolyl, biphenyl, naphthyl, anthryl, furyl, thienyl, benzofuranyl, benzothiophenyl, indolyl and isoindolyl are preferred. Four As may be all the same or partly different. The groups referred to here may take plural positions with respect to the atoms having free valencies. The same will do for the groups referred to hereinbelow.

"$Y^1$" in the formula (1) is a substituted or unsubstituted arylene group, or a substituted or unsubstituted heterocyclic divalent group. Specific examples thereof may include phenylene, tolylene, biphenyldiyl, naphthylene, fluorenediyl, binaphthalendiyl, anthracendiyl, phenanthrendiyl, tihophenediyl, furandiyl, carbazoldiyl, dibenzofurandiyl and so forth. Among these 1,3-phenylene, 5-methyl-1,3-phenylene, 2,7-naphthylene, furan-2,5-diyl and thiophen-2,5-diyl are preferred.

"$Y^2$" in the formula (1) is the group represented by the formula (2) above, a substituted or unsubstituted condensed ring arylene group, or a substituted or unsubstituted heterocyclic divalent group. Specific examples thereof may include biphenyl-4,4'-diyl, 3,3'dimethylbiphenyl-4,4'-diyl, 3,5-dimethylbiphenyl-4,4'-diyl, 3,3',5,5'-tetramethylbiphenyl-4,4'-diyl, 3,3 '-dimethoxybiphenyl-4,4'-diyl, 3,5-dimethoxybiphenyl-4,4'-diyl, 3,3',5,5'-tetramethoxybiphenal-4,4'-diyl, diphenylmethan-4,4'-diyl, stilben-4,4'-diyl, diphenylacetylen-4,4'-diyl, diphenylether-4,4 -diyl, benzophenon-4,4'-diyl, diphenylsulfide-4,4'-diyl, diphenylsulfon-4,4'-diyl, 1,4-naphthylene, fluoren- 1,4-diyl, anthracen-1,4-diyl, furan-2,5-diyl, thiophen-2,5-diyl, isobenzofuran- 1,3-diyl, thieno[2,3-b]thiophen-2,5-diyl. terohenvl-4.4"-diyl, and so forth. Among these, biphenyl-4, 4'-diyl, 3,3'-dimethylbiphenyl-4,4'-diyl, diphenylmethan-4, 4'-diyl, diphenylacetylen-4,4'-diyl, diphenyl ether-4,4'-diyl, diphenyl sulfide-4,4 '-diyl, diphenylsulfon-4,4'-diyl, 1,4-naphthylene, furan-2,5-diyl and thiophen-2,5-diyl are preferred.

Examples of the cyclic tertiary amine compound of the present invention represented by the formula (1) include compounds of the formulae (3) to (26) below.

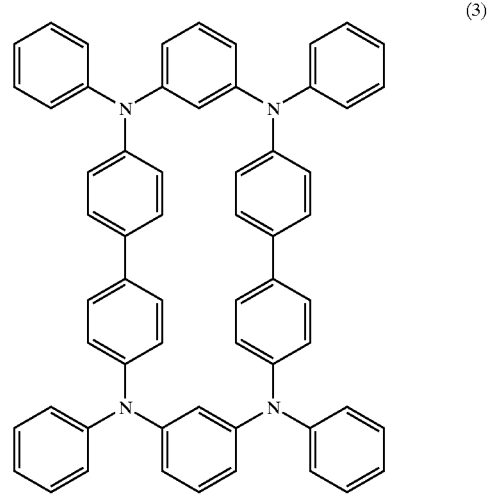

(3)

(4)
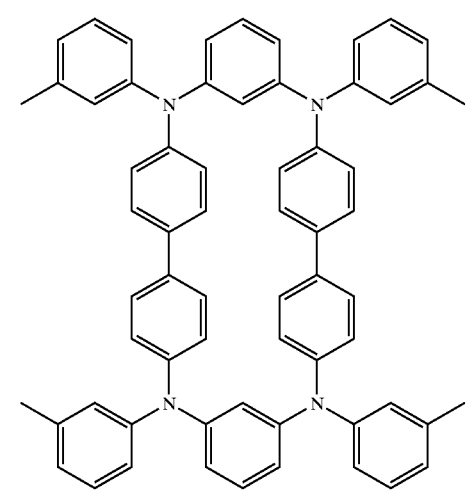
(5)
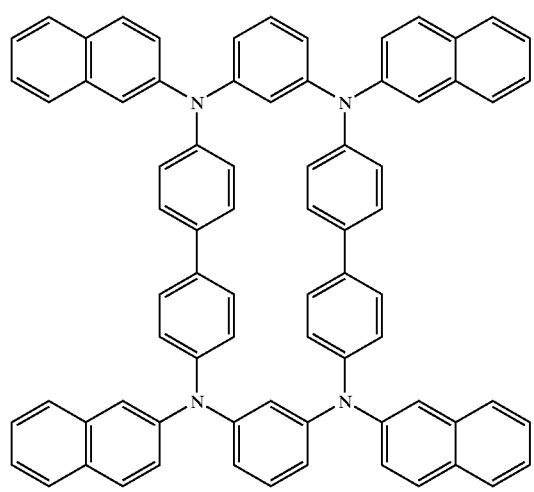
(6)
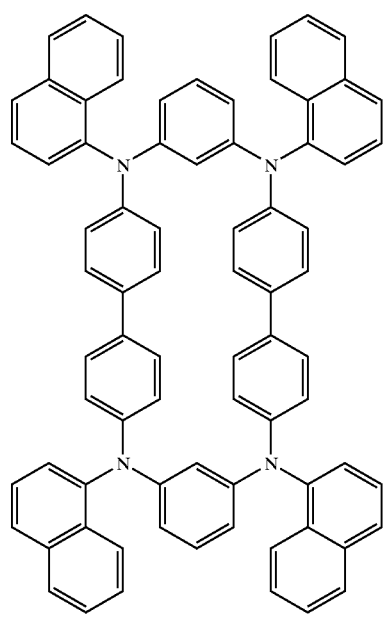
(7)
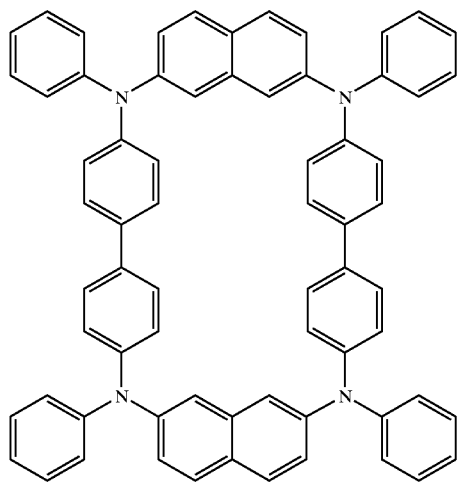
(8)
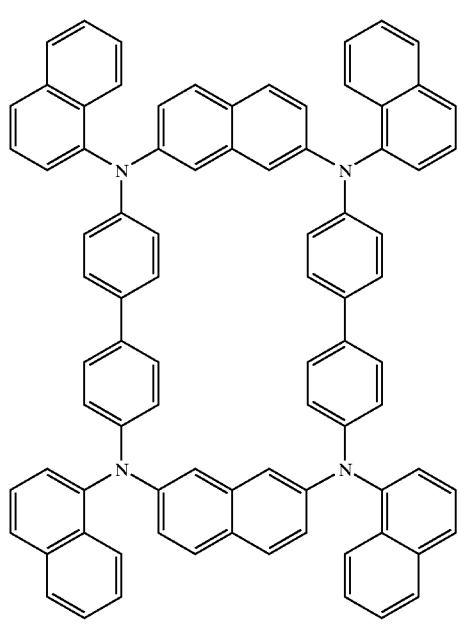
(9)
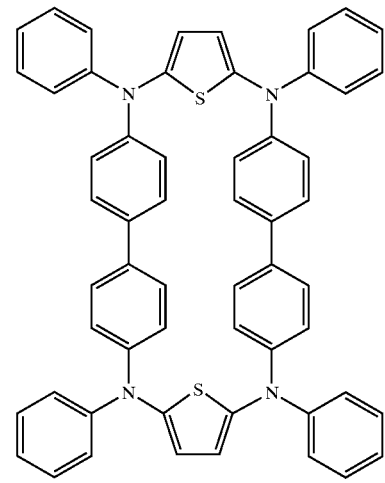

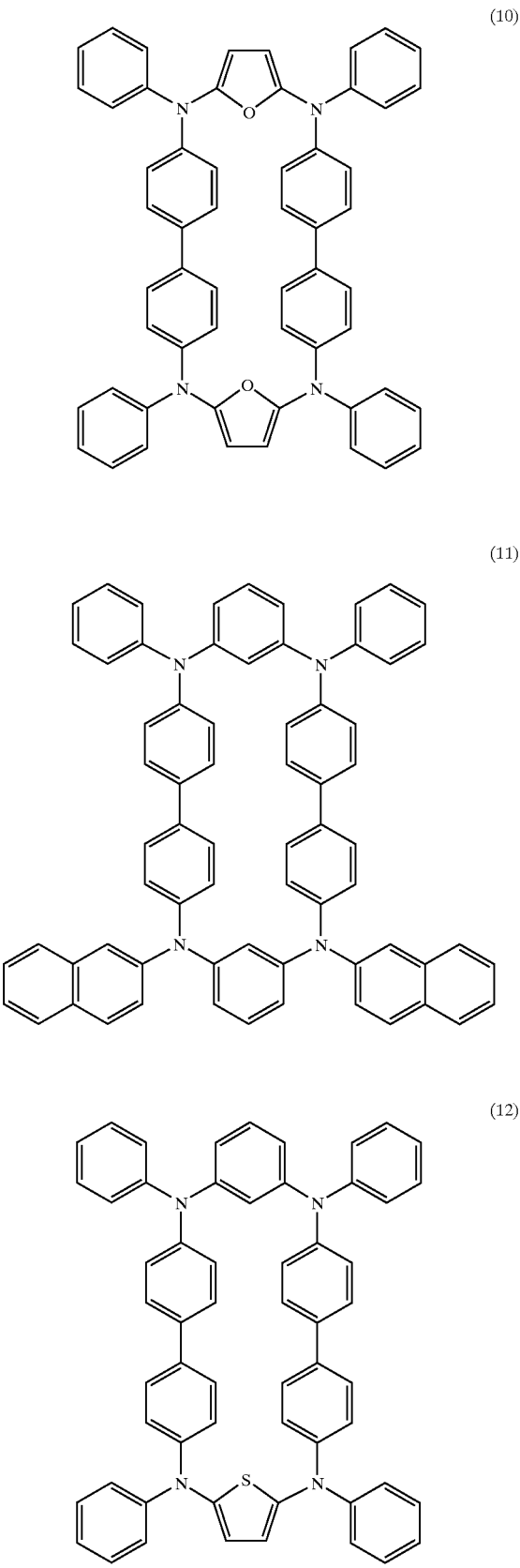
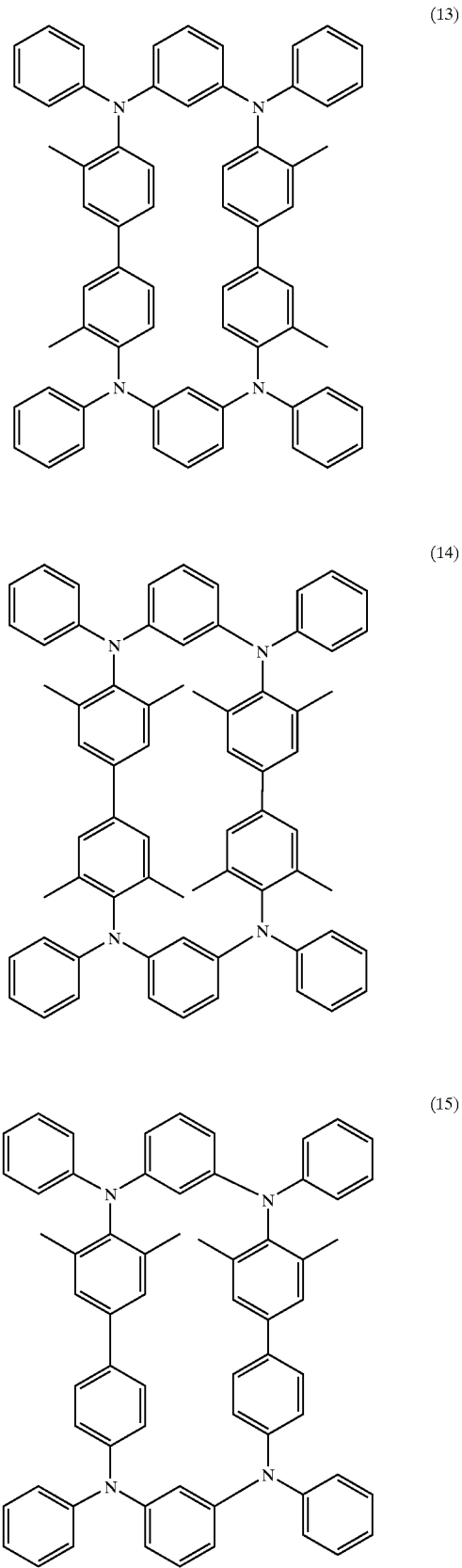

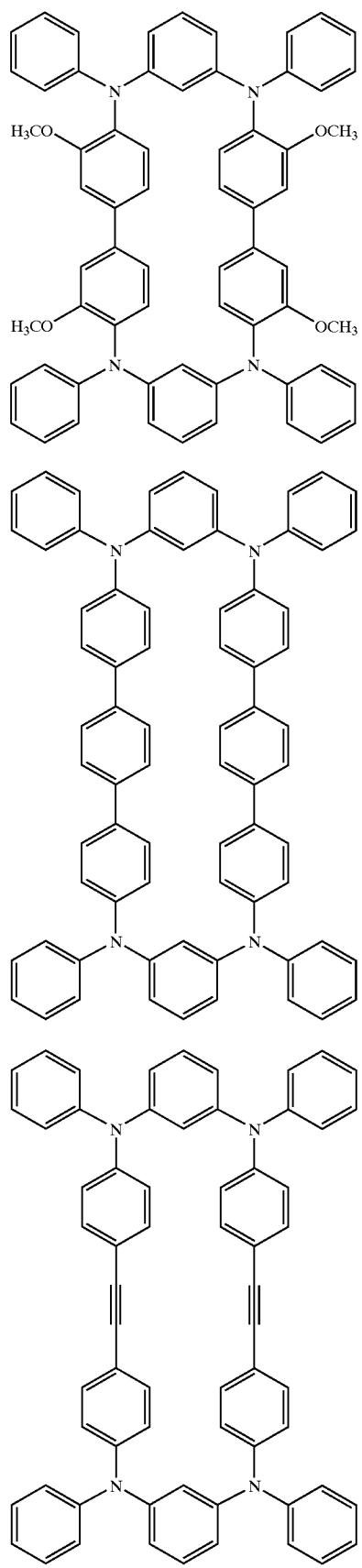
(16)
(17)
(18)
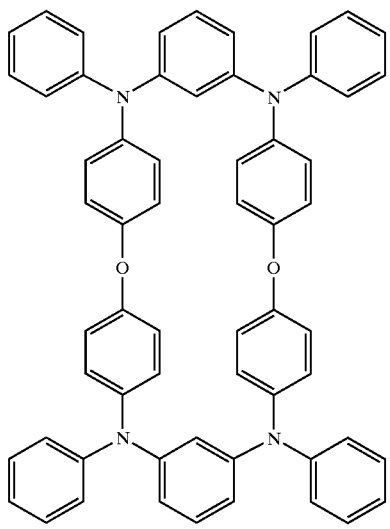
(19)
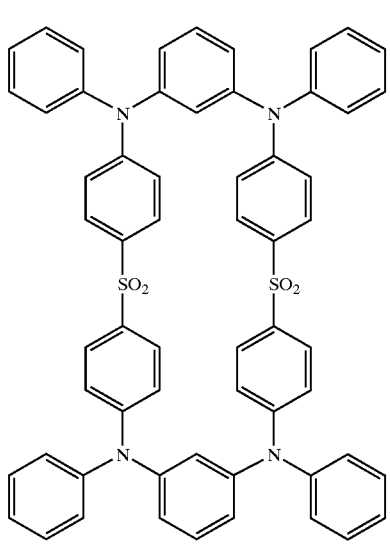
(20)
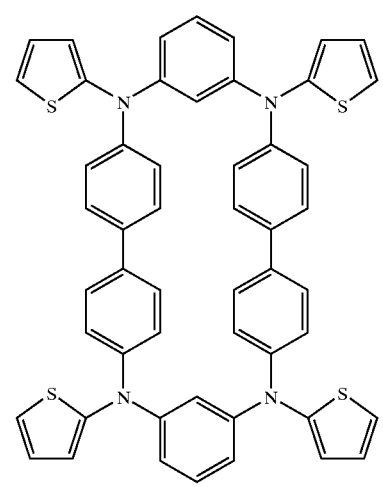
(21)

(22)
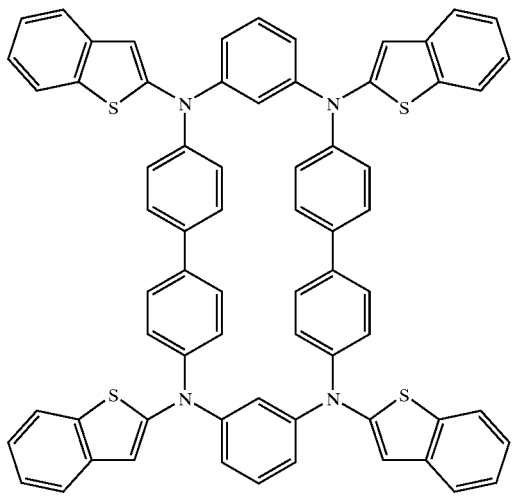

(23)
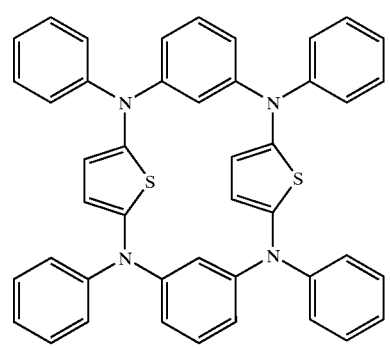

(24)
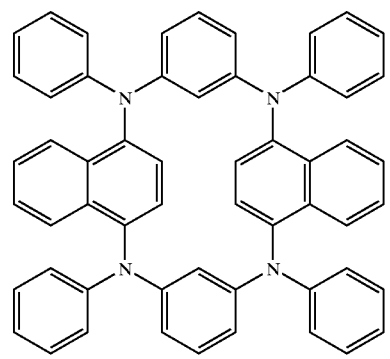

(25)
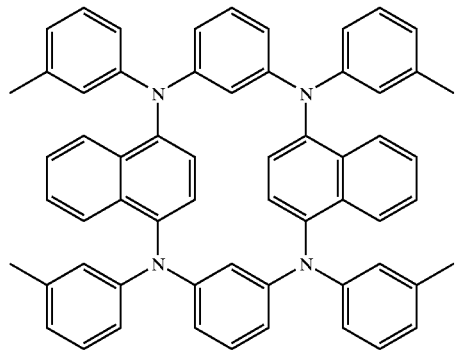

(26)
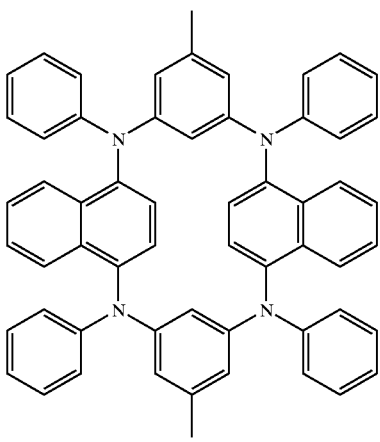

These cyclic tertiary amine compounds can be synthesized by using the known synthetic methods. For example, explanation will be made according to the formula (1). In this case, generally used is a method in which a diamine compound represented by A—NH—$Y^1$—NH—A and a dihalogen compound represented by $Y^2X_2$ (X represents a halogen atom) is reacted by applying a Ullmann reaction. In this method, it is also possible to perform a variation that a diamine compound represented by A—NH—$Y^2$—NH—A and a dihalogen compound represented by $Y^1X_2$ (X has the same meaning as defined above) are reacted. Which one is to be selected may be determined taking into consideration availability of the diamine compound and the dihalogen compound used as starting materials or that as to which is easier to synthesize. In the case where this method is used, a plurality of products will be obtained when all the As are not the same. However, sophisticated procedures such as successive reactions by protecting one of NH groups of the diamine compound and the like enables introduction of different A groups in a single compound.

The Ullmann reaction is a method in which the reaction is performed by heating in a solvent or without solvents in the presence of a base such as potassium carbonate, sodium carbonate, sodium hydrogen carbonate, or sodium hydride. When a solvent is used, N,N-dimethylformamide, nitrobenzene, dimethyl sulfoxide, dichlorobenzene, quinoline or the like may be used. In the present invention, the reaction temperature is 160 to 250° C. In the case where the reactivity is poor, the reaction may be carried out at a higher temperature by using an autoclave, for example. Usually, the reaction is performed by adding a catalyst such as copper powder, copper oxide or copper halide. This is more advantageous than without using a catalyst.

The cyclic tertiary amine compounds of the present invention themselves fluoresce and hence are suitable as a luminescent material. In particular, the cyclic tertiary amine compounds of the present invention emit in blue so that addition of other luminescent materials of different colors such as yellow, green, or red can provide organic EL devices of different luminescent colors.

Further, the organic EL devices of the present invention have not only high efficiencies but also high durabilities when they are stored and when they are driven. This is one of the features of the cyclic tertiary amine compounds of the present invention shown by the formula (1). For the As in the formula (1), aryl groups or heterocyclic groups are preferred to alkyl groups to keep the durability.

The organic EL devices of the present invention may take various types of structures. Basically, an organic layer containing the above-mentioned cyclic tertiary amine compound (hereinafter also referred to cyclic tertiary amine layer) is sandwiched between a pair of electrodes (anode and cathode). Optionally, it may contain in the cyclic tertiary amine layer a hole injection material, a hole transport material, a luminescent material, an electron injection material, an electron transport material or the like usually used in the organic EL devices. Further, in the case where the cyclic tertiary amine layer is used as a luminescent layer, addition of other luminescent material to the luminescent layer can emit a light having a different wavelength or improve luminous efficiency. Furthermore, the hole injection material, hole transport material, luminescent material, electron injection material or electron transport material usually used in organic EL devices may be laminated to the cyclic tertiary amine layer as a hole injection layer, a hole transport layer, a luminescent layer, an electron injection layer or an electron transport layer.

Specific examples of the structure include laminated structures such as (1) anode/cyclic tertiary amine layer/cathode, (2) anode/cyclic tertiary amine layer/luminescent layer/cathode, (3) anode/cyclic tertiary amine layer/luminescent layer/electron injection layer/cathode, (4) anode/hole injection layer/cyclic tertiary amine layer/luminescent layer/electron injection layer/cathode, (5) anode/cyclic tertiary amine layer/hole transport layer/luminescent layer/electron injection layer/cathode, and (6) anode/hole injection layer/cyclic tertiary amine layer/electron injection layer/cathode. In these cases, the hole injection layer and the electron injection layer are not indispensable. However, provision of these layers can improve the luminous efficiency and durability of the device and also prolong the service life of the device.

The organic EL devices of the present invention are preferably supported on substrates regardless of which one of the structures described above it takes. The substrate may be one of any material as far as it has mechanical strength, thermal stability and transparency. For example, glass, transparent plastic film and so forth may be used.

The anode material used in the organic EL devices of the present invention may be metals, alloys, electroconductive compounds and mixtures thereof having work functions greater than 4 eV. Specific examples thereof include metals such as Au, electroconductive transparent materials such as CuI, indium tin oxide (hereinafter abbreviated as "ITO"), $SnO_2$, ZnO, and so forth.

As the cathode material, metals, alloys, electroconductive compounds and mixtures thereof having work functions smaller than 4 eV may be used. Specific examples thereof include aluminum, calcium, magnesium, lithium, magnesium alloys, aluminum alloys and so forth. The alloys may include aluminum/lithium fluoride, aluminum/lithium, magnesium/silver, magnesium/indium and so forth.

To take out electroluminescence of the organic EL devices effectively, at least one of the electrodes is desirably have an optical transmission factor of 10% or more. The sheet resistance of the electrode is preferably several hundreds $\Omega$/square or less. The film thickness may vary depending on the nature of the electrode material but usually it is selected in the range of 10 nm to 1 $\mu$m, preferably 10 to 400 nm. Such an electrode may be fabricated by forming a thin film using the above-mentioned electrode material by a vapor deposition method or a sputtering method.

Hole injection materials and hole transport materials other than the charge transport material used in the organic EL devices of the present invention may be any material optionally selected from the known materials that have been commonly used as the hole transport materials in the field of optoelectric materials and those used in the hole injection layer and the hole transport layer in the organic EL devices. For example, mention may be made of carbazole derivatives (N-phenylcarbazole, polyvinylcarbazole, etc.), triarylamine derivatives, stilbene derivatives (those described on page 1392, 2PB098 in Preliminary Print (II) of Speeches of the $72^{nd}$ Spring Yearly Meeting of Japan Chemical Society), phthalocyanine derivatives (metal-free phthalocyanine, copper phthalocyanine, etc.), polysilanes and so forth. The above-mentioned triarylamine derivative include TPD, polymers having an aromatic tertiary amine in the main chain or in the side chain, 1,1-bis(4-di-p-toly; aminophenyl) cyclohexane, N,N'-dipheny,-N,N'-dinaphthyl-4,4'-diaminobiphenyl (hereinafter abbreviated as "NPD"), 4,4', 4"-tris(N-(3-methylphenyl)-N-phenylamino)triphenyl amine, the compounds disclosed in J. Chem. Soc. Chem. Comm., 2175 (1996), the compounds disclosed in Japanese Patent Application Laid-open Nos. Sho 57-144558, Sho 61-62038, Sho 61-124949, Sho 61-134354, Sho 61-134355, Sho 61-112164, Hei 4-308688, Hei 6-312979, Hei 6-267658, Hei 7-90256, Hei 7-97355, Hei 6-1972, Hei 7-126226, Hei 7-126615, Hei 7-331238, Hei 8-100172, or Hei 8-48656, the starburst amine derivatives disclosed in Adv. Mater., 6, 677 (1994) and so forth.

The hole injection layer and the hole transport layer in the organic EL devices of the present invention may be constructed by one layer containing one or more of the above-mentioned compounds or by one layer that contains one or more of the above-mentioned compounds and the charge transfer material of the present invention. Alternatively, it may be constructed by a plurality of layers containing one or more of the above-mentioned compounds laminated one on another or a plurality of layers containing one or more of the above-mentioned compounds and the charge transport material of the present invention laminated one on another.

The electron injection material and the electron transport material other than the charge transport materials of the present invention used in the organic EL devices of the present invention are not particularly limited and any material can be optionally selected from the known materials that have been commonly used as an electron transport compound in the field of photoconductive material and those used in the electron injection layer and in the electron transport layer in the organic EL devices.

Preferred examples of such electron transport compounds include diphenylquinone derivatives (those disclosed in Denshi Shashin Gakkai-shi, 30 (3), 266 (1991) and so forth), perylene derivatives (those disclosed in J. Apply. Phys., 27, 269 (1988) and so forth), oxadiazole derivatives (those disclosed in the above literature references, Jpn. J. Aplly. Phys. 27, L713 (1988), Appl. Phys. Lett. 55, 1489 (1989) and so forth), thiophene derivatives (those disclosed in Japanese Patent Application Laid-open No. Hei 4-212286 and so forth), triazole derivatives (those disclosed in Jpn. J. Appl. Phys., 32, L917 (1993) and so forth), thiadiazole derivatives (those disclosed in Preliminary Print of the $43^{rd}$ Conference of Japan Polymer Association, (III), P1a007 and so forth), metal complexes of oxine derivatives (Technical Research Report of Japan Electronic Information Communication Society, 92 (311), 43 (1992) and so forth), polymers of quinoxaline derivatives (those disclosed in Jpn. J. Appl. Phys., 33, L250 (1994) and so forth), phenanthroline derivatives (those disclosed in Preliminary Print of the 43$^{rd}$ Symposium of Japan Polymer Association, 14J07 and so forth), and the like.

The luminescent materials other than the electroluminescent materials of the present invention used in the luminescent layer of the organic EL devices of the present invention may be known luminescent materials such as daylight fluorescent materials, fluorescent brighteners, laser dyes, organic scintillators, various fluorimetric reagents as disclosed in Japan Polymer Society, ed.: Polymer Functional Material Series "Optical Functional Materials", Kyoritsu Shuppan (1991), p. 236.

Specifically, polycyclic condensed compounds such as anthracene, phenanthrene, pyrene, chrysene, perylene, coronene, rubrene and quinacridone, oligophenylene based compounds such as quarter phenyl, scintillators for liquid scintillation such as 1,4-bis(2-methylstyryl)benzene, 1,4-bis(4-methylstyryl)benzene, 1,4-bis(4-phenyl-5-oxazolyl)benzene, 1,4-bis(5-phenyl-2-oxazolyl)benzene, 2,5-bis(5-tertiary-butyl-2-benzoxazolyl)thiophene, 1,4-diphenyl-1,3-butadiene, 1,6-diphenyl-1,3,5-hexatriene and 1,1,4,4-tetraphenyl-1,3-butadiene, the metal complexes of oxine derivatives disclosed in Japanese Patent Application Laid-open No. Sho 63-264692, coumarin dyes, dicyanomethyl-enepyrane dyes, dicyanomethylenethiopyrane dyes, polymethyne dyes, oxobenzanthracene dyes, xanthene dyes, carbostyryl dyes, and perylene dyes, the oxazine based compounds disclosed in German Patent No. 2,534,713, the stilbene derivatives disclosed in Preliminary Print of Speeches in 40$^{th}$ Applied Physics Related Joint Meeting, 1146 (1993), the spiro compounds disclosed in Japanese Patent Application Laid-open No. Hei 7-278537 and the oxadiazole based compounds disclosed in Japanese Patent Application Laid-open No. Hei 4-363891, and so forth are preferred. Also, the publicly known phosphorescent compounds, for example, iridium complexes, platinum complexes, europium complexes and so forth as disclosed in Preliminary Print of Speeches in the 9$^{th}$ Japan Applied Physics Society Meeting (2001) p.17 and "Organic EL Materials and Displays," CMC (2001) p.170 are preferred as the luminescent materials.

Each layer that constitutes the organic EL device of the present invention can be formed by forming a thin film from the material to be used for constituting each layer by a known method such as a vapor deposition method, a spin-coating method or a casting method. The film thickness of each layer thus formed is not particularly limited and may be selected appropriately depending on the nature of the material. Usually, it is selected in the range of 2 to 5,000 nm.

As for the method for forming a thin film of cyclic tertiary amine compound, a vapor deposition method is preferable from the viewpoint that uniform films can be readily obtained and pinholes are difficult to occur. When thin films are formed by using a vapor deposition method, the vapor deposition conditions may vary depending on the type of the cyclic tertiary amine compound, a target crystal structure and association structure of a molecule accumulated film. Generally, it is preferable that the conditions be appropriately selected in the following ranges: a boat heating temperature of 50 to 400° C., a degree of vacuum of $10^{-6}$ to $10^{-3}$ Pa, a vapor deposition rate of 0.01 to 50 nm/second, a substrate temperature of −150 to +300° C., and a film thickness of 5 nm to 5 μm.

Next, as one example of the method for making an organic EL device using the cyclic tertiary amine compound of the present invention, a method for making an organic EL device composed of the above-mentioned structure of anode/cyclic tertiary amine compound/cathode will be described. That is, on a suitable substrate a thin film of an anode substance is formed by a vapor deposition method so as to have a film thickness in the range of 1 μm or less, preferably 10 to 200 nm to make an anode. Then a thin film of a cyclic tertiary amine compound is formed on the anode to provide a luminescent layer. Further, a thin film of a cathode substance is formed on the luminescent layer by a vapor deposition method so as to have a film thickness of 1 μm or less to provide a cathode. Thus, the target organic EL device is obtained. In making the above-mentioned organic EL device, the order of the making may be in reverse to make a cathode, a luminescent layer, and an anode in this order.

When applying direct current to the thus-obtained organic EL device, the current may be applied such that the anode has a polarity of "+" and the cathode has a polarity of "−". When applying a voltage of about 2 to 40 V, emission is observed in the transparent or translucent electrode side (anode or cathode, or the both). The organic EL device can also emit light when alternating current is applied. The waveform of the applied alternating current may be optional.

Hereinafter, the present invention will be illustrated in more detail with reference to examples. However, the present invention should not be limited thereto.

Synthesis Example 1
(Synthesis of Compound of the Above Formula (3) (Hereinafter Abbreviated TACB))

0.91 g of N,N'-diphenyl-m-phenylenediamine, 2.8 g of 4,4'-diiodobiphenyl, 1.75 g of copper powder, 7.77 g of potassium carbonate, 0.19 g of 18-crown-6, and 175 ml of o-dichlorobenzene were charged in a flask and refluxed at 180° C. for 5 hours in a nitrogen atmosphere. Thereafter, a solution of 0.91 g of N,N'-diphenyl-m-phenylenediamine in 175 ml of o-dichlorobenzene was dropped and the mixture was refluxed at 180° C. for 48 hours. After completion of the reaction, the reaction solution was cooled, solids were filtered off, and the filtrate was concentrated under reduced pressure, and then the residue was washed with THF (tetrahydrofuran). Then the extraction of the product with 90 ml of toluene by a Soxhlet extraction method afforded 1 g of white crystals of the target compound. Elemental analysis as $C_{60}H_{44}N_4$ gave the following results.

|  | C (%) | H (%) | N (%) |
| --- | --- | --- | --- |
| Calculated Value | 87.77 | 5.41 | 6.82 |
| Found Value | 87.80 | 5.35 | 6.85 |

The fluorescent color of the compound in toluene was bluish.

By appropriate selection of starting materials, other cyclic tertiary amine compounds can be synthesized in quite the same manner as described in this Synthesis Example.

EXAMPLE 1

A 25 mm×75 mm×1.1 mm glass substrate on which ITO was deposited to a thickness of 50 nm (produced by Tokyo Sanyo Vacuum Co., Ltd.) was used as a transparent support substrate. The transparent support substrate was fixed onto a substrate holder of a commercially available vapor deposition apparatus (produced by Shinku Kiko Co., Ltd.). Then, a molybdenum-made vapor deposition boat containing TACB synthesized in Synthesis Example 1 above, a molybdenum-made vapor deposition boat containing tris(8-hydroxyquinoline)aluminum (hereinafter abbreviated as "ALQ"), a molybdenum-made vapor deposition boat containing lithium fluoride, and a tungsten-made vapor deposition boat containing aluminum were attached. A vacuum vessel was depressurized to a pressure of $1\times10^{-3}$ Pa and TACB-containing vapor deposition boat was heated so that TACB was deposited to a film thickness of 50 nm to form a hole transport layer. Then, the ALQ-containing vapor deposition boat was heated so that ALQ was deposited to a film thickness of 50 nm to form a luminescent layer. The deposition rates were each 0.1 to 0.2 nm/second. Thereafter, the lithium fluoride-containing vapor deposition boat was heated so that lithium fluoride was deposited at a deposition rate of 0.003 to 0.01 nm/second so as to have a film thickness of 0.5 nm. Then, the aluminum-containing vapor deposition boat was heated and deposited at a deposition rate of 0.2 to 0.5 nm/second so as to have a film thickness of 100 nm. Thus an organic EL device was obtained. A direct current voltage of about 3.6 V was applied between the ITO electrode as an anode and the lithium fluoride/aluminum electrode as a cathode. As a result, a current of about 3.6 mA/cm$^2$ flowed to emit a green light having a wavelength of 526 nm at a luminance of about 100 cd/m$^2$ and a luminous efficiency of 2.4 lm/W. Continuous driving of the device at a constant current under the condition of initial intensity of 100 cd/M$^2$ in dry nitrogen revealed that the half service life was about 1,500 hours. Also, when heating the device at 100° C., emission of light was observed.

Comparative Example 1

An organic EL device was fabricated in the same manner as in Example 1 except that TACB used in Example 1 was replaced by NPD. A direct current voltage of about 4 V was applied between an ITO electrode as an anode and a lithium fluoride/aluminum electrode as a cathode. As a result, a current of about 4 mA/cm$^2$ flowed to emit a light at a luminance of about 100 cd/m$^2$ and a luminous efficiency of 1.9 lm/W. Continuous driving of the device at a constant current under the condition of the initial luminance of 100 cd/m$^2$ in dry nitrogen revealed that the half service life was about 960 hours. Also, when heating the device at 100° C., no emission of light was observed.

EXAMPLE 2

In the same manner as in Example 1, the transparent support substrate was fixed to the substrate holder of the vapor deposition apparatus. Then, a molybdenum-made vapor deposition boat containing TACB synthesized in Synthesis Example 1 above, a molybdenum-made vapor deposition boat containing NPD, a molybdenum-made vapor deposition boat containing ALQ, a molybdenum-made vapor deposition boat containing lithium fluoride, and a tungsten-made vapor deposition boat containing aluminum were attached. The vacuum vessel was depressurized to a pressure of $1\times10^{-3}$ Pa and TACB-containing vapor deposition boat was heated so that TACB was deposited to a film thickness of 40 nm to form a hole injection layer. Subsequently, the NPD-containing vapor deposition boat was heated so that NPD was deposited to a film thickness of 10 nm to form a hole transport layer. Then, the ALQ-containing vapor deposition boat was heated so that ALQ was deposited to a film thickness of 50 nm to form a luminescent layer. The deposition rates were each 0.1 to 0.2 nm/second. Thereafter, the lithium fluoride-containing vapor deposition boat was heated so that lithium fluoride was deposited at a deposition rate of 0.003 to 0.01 nm/second so as to have a film thickness of 0.5 nm. Subsequently, the aluminum-containing vapor deposition boat was heated at a deposition rate of 0.2 to 0.5 nm/second so as to have a film thickness of 100 nm. Thus an organic EL device was obtained. A direct current voltage of about 4 V was applied between an ITO electrode as an anode and an lithium fluoride/aluminum electrode as a cathode. As a result, a current of about 3 mA/cm$^2$ flowed to emit a green light having a wavelength of 520 nm at an intensity of about 100 cd/m$^2$ and a luminous efficiency of 2.6 lm/W.

EXAMPLE 3

In the same manner as in Example 1, the transparent support substrate was fixed to the substrate holder of the vapor deposition apparatus. Then, a molybdenum-made vapor deposition boat containing TACB synthesized in Synthesis Example 1 above, a molybdenum-made vapor deposition boat containing 9,9'-spirobisilafluorene, a molybdenum-made vapor deposition boat containing lithium fluoride, and a tungsten-made vapor deposition boat containing aluminum were attached. The vacuum vessel was depressurized to a pressure of $1\times10^{-3}$ Pa and TACB-containing vapor deposition boat was heated so that TACB was deposited to a film thickness of 50 nm to form a hole transporting luminescent layer. Subsequently, the 9,9'-spirobisilafluorene-containing vapor deposition boat was heated so that 9,9'-spirobisilafluorene was deposited to a film thickness of 50 nm to form an electron transport layer. The vapor deposition rates were each 0.1 to 0.2 nm/second. Thereafter, the lithium fluoride-containing vapor deposition boat was heated so that lithium fluoride was deposited at a deposition rate of 0.003 to 0.01 nm/second so as to have a film thickness of 0.5 nm. Subsequently, the aluminum-containing vapor deposition boat was heated at a deposition rate of 0.2 to 0.5 nm/second so as to have a film thickness of 100 nm. Thus an organic EL device was obtained. A direct current voltage of 6 V was applied between an ITO electrode as an anode and an lithium fluoride/aluminum electrode as a cathode. As a result, emission of a blue light having a wavelength of 430 nm was observed.

EXAMPLE 4

In the same manner as in Example 1, the transparent support substrate was fixed to the substrate holder of the vapor deposition apparatus. Then, a molybdenum-made vapor deposition boat containing TACB synthesized in Synthesis Example 1 above, a molybdenum-made vapor deposition boat containing 4,4',4"-tris(N-(3-methylphenyl)-N-phenylamino) triphenylamine, a molybdenum-made vapor deposition boat containing ALQ, a molybdenum-made vapor deposition boat containing lithium fluoride, and a tungsten-made vapor deposition boat containing aluminum were attached. The vacuum vessel was depressurized to a pressure of $1\times10^{-3}$ Pa and 4,4',4"-tris(N-(3-methylphenyl)-N-phenylamino) triphenylamine-containing vapor deposition boat was heated so that 4,4',4"-tris(N-(3-methylphenyl)-N-phenylamino) triphenylamine was deposited to a film thickness of 40 nm to form a hole injection layer. Subsequently, the TACB-containing vapor deposition boat was heated so that TACB was deposited to a film thickness of 10 nm to form a hole transport layer. Then, the ALQ-containing vapor deposition boat was heated so that ALQ was deposited to a film thickness of 50 nm to form a luminescent layer. The deposition rates were each 0.1 to 0.2 nm/second. Thereafter, The lithium fluoride-containing vapor deposition boat was heated so that lithium fluoride was deposited at a deposition rate of 0.003 to 0.01 nm/second so as to have a film thickness of 0.5 nm. Subsequently, the aluminum-containing vapor deposition boat was heated at a deposition rate of 0.2 to 0.5 nm/second so as to have a film thickness of 100 nm. Thus an organic EL device was obtained. A direct current voltage of 3.5 V was applied between an ITO electrode as an anode and a lithium fluoride/aluminum electrode as a cathode. As a result, a current of about 3.5 mA/cm$^2$ flowed to emit a green light having a wavelength of 523 nm at a luminance of about 100 cd/m$^2$ and a luminous efficiency of 2.5 lm/W.

As described above, use of the cyclic tertiary amine compounds of the present invention as a hole transport material, a hole injection material or an organic luminescent material can provide organic EL devices having high luminous efficiency and a prolonged service life. That is, the organic EL devices of the present invention can increase luminous efficiency, prolong the service life and display in full color easily because they use the charge transport material and the luminescent material containing the cyclic tertiary amine compounds as a hole transport layer, a hole injection layer and/or a luminescent layer. Therefore, use of the organic EL devices of the present invention enables production of a high efficient display apparatus such as a full color display.

What is claimed is:

1. An organic electroluminescent device comprising a pair of electrodes and at least one layer, wherein the layer contains a cyclic tertiary amine compound represented by a formula (1),

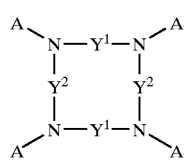

(1)

wherein A represents an alkyl group having 1 to 6 carbon atoms, a substituted or unsubstituted aryl group, a substituted or unsubstituted aralkyl group, or a substituted or unsubstituted heterocyclic group, and four As may be all the same or partly different; Y$^1$ represents a substituted or unsubstituted arylene group, or a substituted or unsubstituted heterocyclic divalent group; Y$^2$ represents a group represented by a formula (2), a substituted or unsubstituted condensed ring arylene group, or a substituted or unsubstituted heterocyclic divalent group,

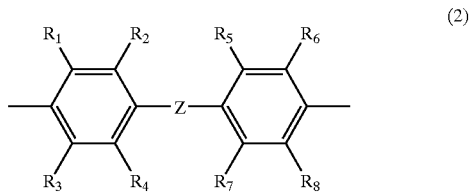

(2)

wherein R$_1$ to R$_8$ in the formula (2) independently represents a hydrogen atom, a halogen atom, an alkyl or alkoxy group having 1 to 6 carbon atoms, an aryl group or a heterocyclic group; and Z represents single bond, an arylene group, —CH$_2$—, —CH=CH—, —C≡C—, —C(CH$_3$)$_2$—, —CO—, —O—, —S—, or —SO$_2$—.

2. The organic electroluminescent device according to claim 1, wherein the cyclic tertiary amine compound is contained in a hole transport layer.

3. The organic electroluminescent device according to claim 1, wherein the cyclic tertiary amine compound is contained in a luminescent layer.

4. The organic electroluminescent device according to claim 1, wherein the cyclic tertiary amine compound is contained in a hole injection layer.

* * * * *